US011406767B2

(12) United States Patent
Baumeyer et al.

(10) Patent No.: US 11,406,767 B2
(45) Date of Patent: Aug. 9, 2022

(54) FEEDBACK MECHANISM FOR AN INJECTION DEVICE

(71) Applicant: Sanofi-Aventis Deutschland GMBH, Frankfurt am Main (DE)

(72) Inventors: Martin Baumeyer, Rüsselsheim (DE); Peter Nober, Rüsselsheim (DE); Matthias Rau, Rüsselsheim (DE); Winfried Huthmacher, Rüsselsheim (DE); Markus Janiak, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 598 days.

(21) Appl. No.: 16/346,352

(22) PCT Filed: Oct. 12, 2017

(86) PCT No.: PCT/EP2017/076048
§ 371 (c)(1),
(2) Date: Apr. 30, 2019

(87) PCT Pub. No.: WO2018/082886
PCT Pub. Date: May 11, 2018

(65) Prior Publication Data
US 2019/0269856 A1 Sep. 5, 2019

(30) Foreign Application Priority Data
Nov. 1, 2016 (EP) ..................... 16196675

(51) Int. Cl.
*A61M 5/315* (2006.01)
*A61M 5/20* (2006.01)

(52) U.S. Cl.
CPC ........ *A61M 5/3157* (2013.01); *A61M 5/2033* (2013.01); *A61M 2205/43* (2013.01); *A61M 2205/581* (2013.01); *A61M 2205/582* (2013.01)

(58) Field of Classification Search
CPC .............. A61M 5/2033; A61M 5/3157; A61M 5/1452; A61M 5/20; F04B 43/02
See application file for complete search history.

(56) References Cited

U.S. PATENT DOCUMENTS 5,279,607 A * 1/1994 Schentag ............. A61B 5/0031
604/114
6,620,133 B1 9/2003 Steck
(Continued)

FOREIGN PATENT DOCUMENTS

| CN | 101641125 | 2/2010 |
| CN | 102137692 | 7/2011 |

(Continued)

OTHER PUBLICATIONS

International Preliminary Report on Patentability in International Appln. No. PCT/EP2017/076048, dated May 7, 2019, 9 pages.
(Continued)

*Primary Examiner* — Manuel A Mendez
(74) *Attorney, Agent, or Firm* — Fish & Richardson P.C.

(57) ABSTRACT

A feedback mechanism for an injection device that is configured to deliver a medicament to a user is described. The feedback mechanism has a biasing member that is arranged to apply a force to a delay element, and the delay element is configured to deform and/or break under the force. The feedback mechanism also includes an indicator arranged to generate user feedback after the delay element is deformed and/or broken. The delay element is configured to deform and/or break at a time after the force is applied by the
(Continued)

biasing member to create a delay before the user feedback is generated.

21 Claims, 8 Drawing Sheets

(56) References Cited

U.S. PATENT DOCUMENTS

| | | | |
|---|---|---|---|
| 2011/0208125 | A1 | 8/2011 | Larsen et al. |
| 2013/0317432 | A1 | 11/2013 | Fabien et al. |
| 2016/0008549 | A1 | 1/2016 | Plumptre et al. |
| 2016/0193415 | A1 | 7/2016 | Cowe |

FOREIGN PATENT DOCUMENTS

| | | |
|---|---|---|
| CN | 103143082 | 6/2013 |
| CN | 105025965 | 11/2015 |
| CN | 105451792 | 3/2016 |
| CN | 105960254 | 9/2016 |
| GB | 2516896 | 2/2015 |
| JP | 2015-517369 | 6/2015 |
| JP | 2016-509900 | 4/2016 |
| JP | 2016-528983 | 9/2016 |
| WO | WO 1999/015214 | 4/1999 |
| WO | WO 2008/112472 | 9/2008 |
| WO | WO 2010/023303 | 3/2010 |
| WO | WO 2010/035059 | 4/2010 |
| WO | WO 2011/123024 | 10/2011 |
| WO | WO 2014/139916 | 9/2014 |
| WO | WO 2015/019071 | 2/2015 |
| WO | WO 2015/113968 | 8/2015 |
| WO | WO 2015/185311 | 12/2015 |
| WO | WO 2016/071174 | 5/2016 |
| WO | WO 2016/120587 | 8/2016 |

OTHER PUBLICATIONS

International Search Report and Written Opinion in International Appln. No. PCT/EP2017/076048, dated Dec. 11, 2017, 14 pages.

\* cited by examiner

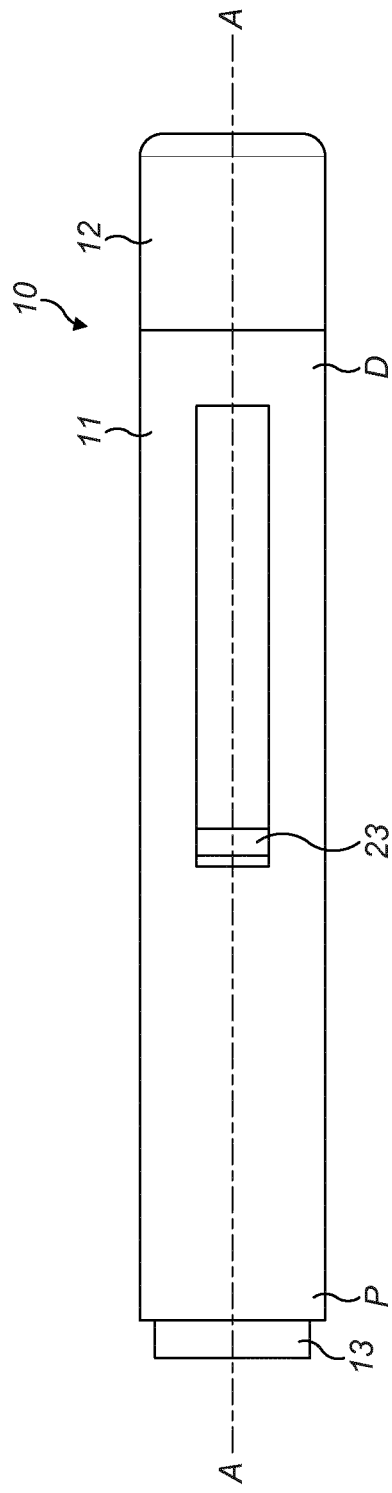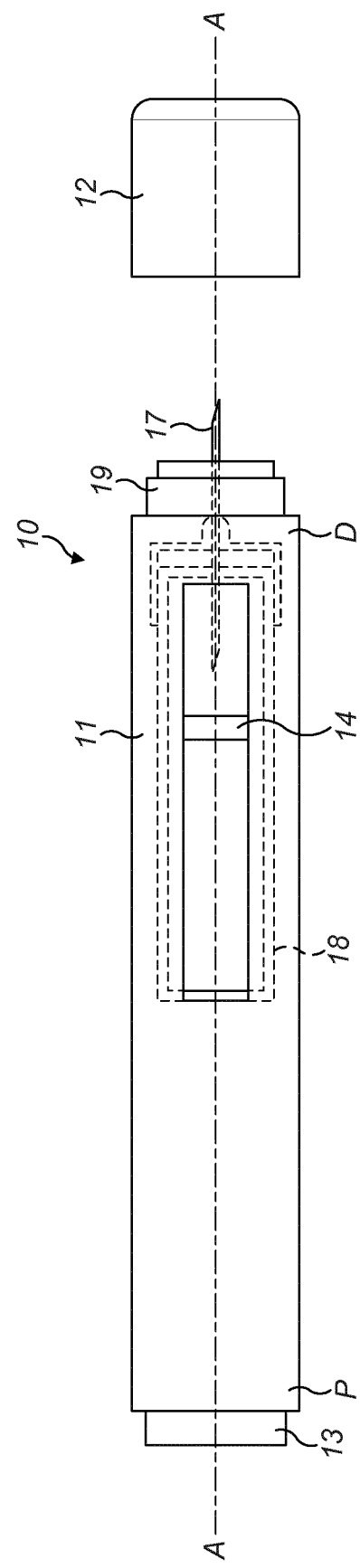
FIG. 1A
FIG. 1B

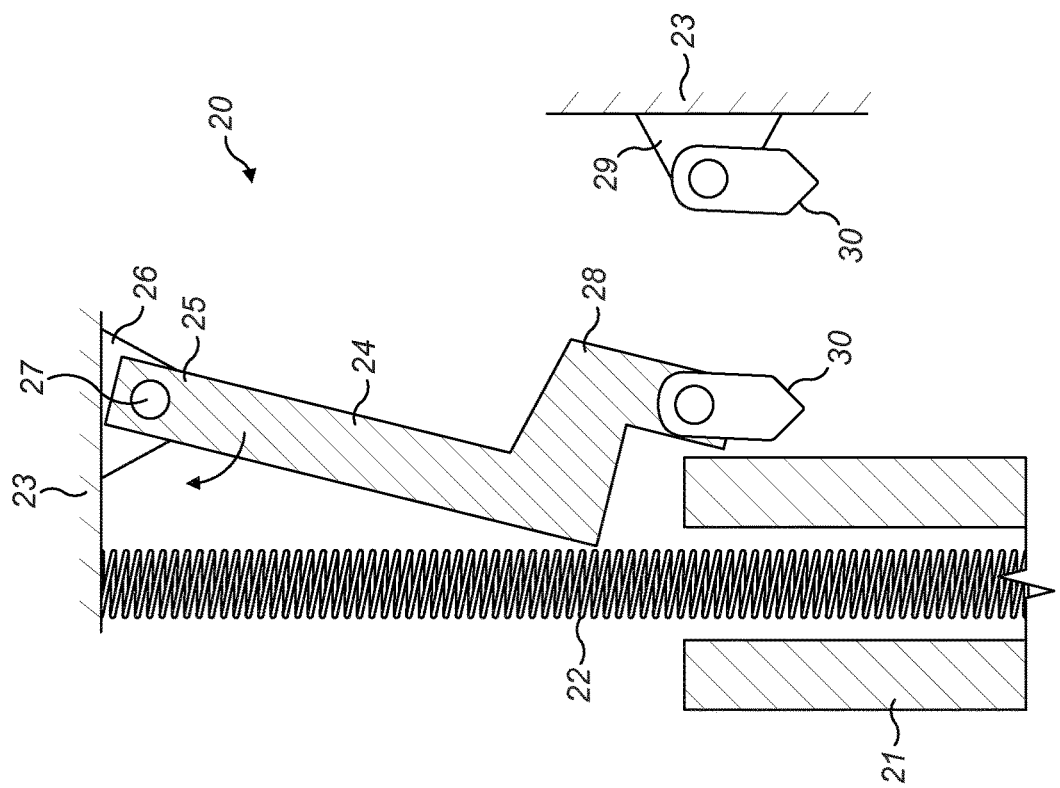
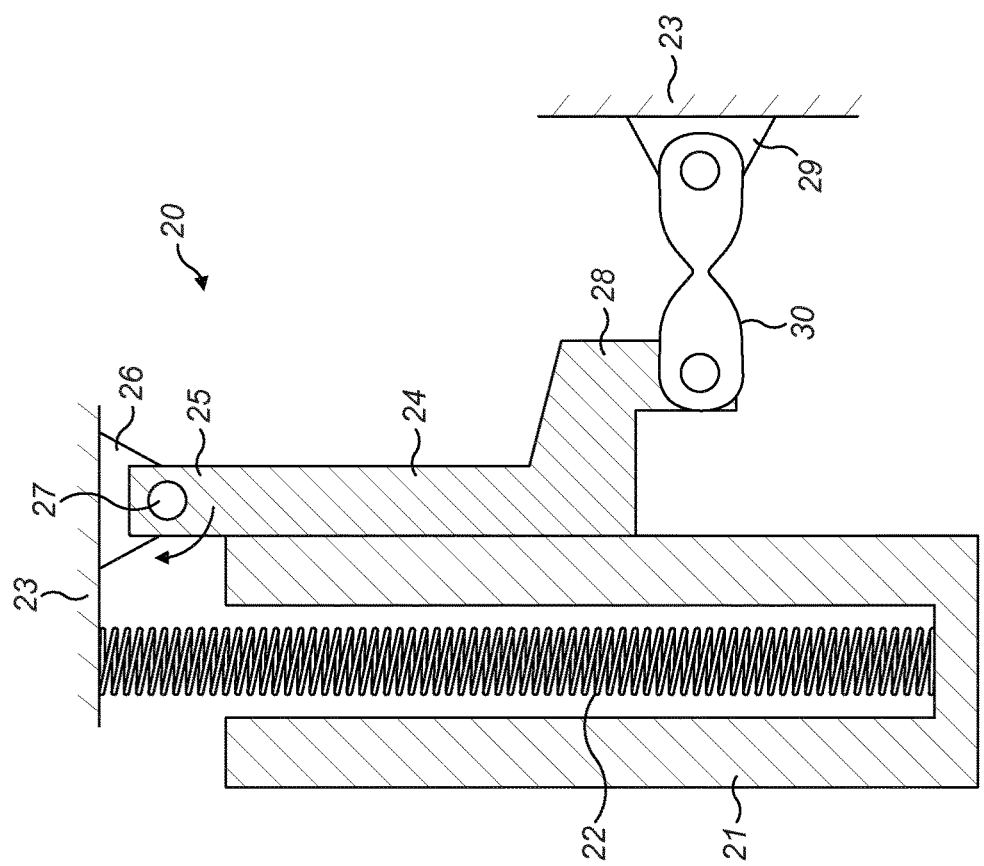

FEEDBACK MECHANISM FOR AN INJECTION DEVICE

CROSS REFERENCE TO RELATED APPLICATIONS

The present application is the national stage entry of International Patent Application No. PCT/EP2017/076048, filed on Oct. 12, 2017, and claims priority to Application No. EP 16196675.9, filed on Nov. 1, 2016, the disclosures of which are incorporated herein by reference.

TECHNICAL FIELD

The present disclosure relates to a feedback mechanism for an injection device.

BACKGROUND

Injection devices, such as auto-injectors, typically have a syringe into which a plunger is pushed to dispense medicament from the syringe into the patient via a needle. The injection process is completed when the plunger has been pushed the appropriate distance into the syringe. It is known to provide a feedback mechanism for indicating to the user when the appropriate volume of medicament has been injected.

SUMMARY

It is an object of the present disclosure to provide a feedback mechanism for an injection device that provides delayed user feedback.

According to a first aspect, there is provided a feedback mechanism for an injection device, said injection device being configured to deliver a medicament to a user, the feedback mechanism comprising:
  a biasing member arranged to apply a force to a delay element, and the delay element being configured to deform and/or break under said force; and,
  an indicator arranged to generate user feedback after the delay element is deformed and/or broken;
  wherein the delay element is configured to deform and/or break at a time after the force is applied by the biasing member to create a delay before the user feedback is generated.

The delay element may comprise a member having a narrow section configured to be deformed and/or broken by the force of the biasing member.

The delay element may comprise an elastically deformable member configured to be deformed and/or broken by the force of the biasing member.

Alternatively, the delay element may comprise a plastically deformable member configured to be deformed and/or broken by the force of the biasing member.

The delay element may comprise a flexible tether configured to be deformed and/or broken by the force of the biasing member.

The feedback mechanism may also comprise a moveable member, and the delay element may be attached to the moveable member and to a fixing. The biasing member may urge the moveable member relative to said fixing such that a force is applied to the delay element.

The indicator may comprise the moveable member, which generates feedback for said user after the delay element is deformed and/or broken and the moveable member moves.

The moveable member may comprise an arm pivotally mounted to a pivot, and the biasing member may be arranged to urge the arm to rotate about the pivot.

The moveable member may comprise a plate, and the biasing member may be arranged to act on the plate.

The indicator may comprise a sound generator arranged to be impacted by the moveable member after the delay element is deformed and/or broken to generate a sound.

The indicator may comprises a pre-stressed element disposed such that the moveable member holds the pre-stressed element in a deflected state until the moveable member is moved, at which point the pre-stressed element moves to a non-deflected state and generates user feedback.

The feedback mechanism may further comprise a holding mechanism arranged to hold the moveable member such that the delay element is not deformed or broken, and the holding mechanism may be further arranged to release the moveable member so that the delay element is deformed and/or broken by the force of the biasing member.

The holding mechanism may be configured to release the moveable member after said injection device has completed delivery of medicament to said user.

The holding mechanism may comprise a plunger of said injection device.

According to another aspect, there is also provided an injection device comprising a medicament delivery mechanism having a reservoir and a plunger that moves to displace medicament from the reservoir for delivery to a user during use of the injection device, and a feedback mechanism described above. During use the plunger may move from a first position to a second position. The first position may correspond to a starting position of the plunger. The second position may correspond to the position of the plunger after the injection device has completed delivery of medicament to said user.

In one example, the feedback mechanism may comprise a moveable member that is attached to the delay element, and the biasing member may apply a force to the moveable member such that a force is applied to the delay element.

The plunger may be arranged such that in the first position the plunger engages the movable member to prevent movement of the movable member, and in the second position the plunger disengages the movable member.

In one example, the delay element may be attached to the movable member and to a fixing. Alternatively, the delay element may be attached to the movable member and to the plunger.

The moveable member may comprise a plate, and the biasing member may be arranged to act on the plate.

The injection device may further comprise a locking arm that engages the plate, the locking arm being pivotally mounted such that in the first position the plunger prevents rotation of the locking arm and the plate is retained by the locking arm, and in the second position the locking arm is free to rotate and release the plate.

The delay element may be arranged to resist rotation of the locking arm until the delay element is deformed and/or broken.

The syringe may optionally contain a medicament.

In one example, there is provided an injection device comprising a medicament delivery mechanism and a feedback mechanism. The medicament delivery mechanism may comprise a reservoir and a plunger that moves during use from a first position to a second position to displace medicament from the reservoir for delivery to a user during use of the injection device. The feedback mechanism may comprise a movable member, a biasing member, and a delay element, wherein the biasing member is arranged to act on the movable member such that a force is applied to the delay element, and the delay element is configured to deform and/or break at a time after the force is applied by the biasing member. The feedback mechanism may also comprise an indicator arranged to generate user feedback after the delay element is deformed and/or broken. The plunger can be arranged such that in the first position the plunger prevents movement of the movable member, and in the second position the plunger releases the movable member such that said force is applied to the delay member by the biasing member.

According to a further aspect, there is also provided a method of using an injection device, the method comprising:
  delivering a medicament to a user;
  applying a force to a delay element to deform and/or break the delay element; and,
  generating user feedback after the delay element has been deformed and/or broken;
  wherein a delay is provided such that the delay element is deformed and/or broken at a time after the force is applied.

These and other aspects will be apparent from and elucidated with reference to the embodiments described hereinafter.

BRIEF DESCRIPTION OF THE FIGURES

Embodiments will now be described, by way of example only, with reference to the accompanying drawings, in which:

FIG. 1A is a schematic side view of an injector device and a removable cap;

FIG. 1B is a schematic side view of the injector device of FIG. 1A, with the cap removed from the housing;

FIG. 2A is a cross-sectional side view of a delay mechanism for an injection device, the delay mechanism having a pivotally mounted arm and a delay element, the delay mechanism shown before the injection device has been used;

FIG. 2B is a cross-section side view of the delay mechanism of FIG. 2A, shown after the injection device has been used;

DETAILED DESCRIPTION

Figure 3A:
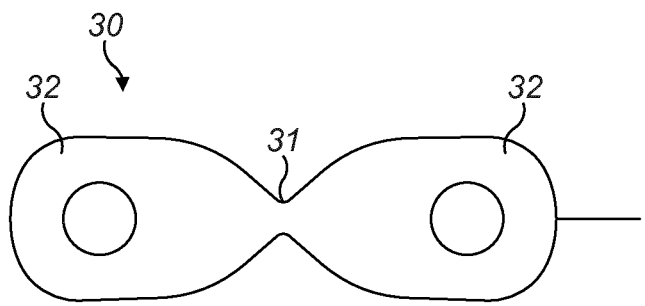
FIGS. 3A to 3C show different examples of delay elements.

A drug delivery device, as described herein, may be configured to inject a medicament into a patient. For example, delivery could be sub-cutaneous, intra-muscular, or intravenous. The user of such a device could be a patient or care-giver, such as a nurse or physician, and can include various types of safety syringe, pen-injector, or auto-injector. The device can include a cartridge-based system that requires piercing a sealed ampule before use. Volumes of medicament delivered with these various devices can range from about 0.5 ml to about 2 ml. Yet another device can include a large volume device ("LVD") or patch pump, configured to adhere to a patient's skin for a period of time (e.g., about 5, 15, 30, 60, or 120 minutes) to deliver a "large" volume of medicament (typically about 2 ml to about 10 ml).

In combination with a specific medicament, the presently described devices may also be customized in order to operate within required specifications. For example, the device may be customized to inject a medicament within a certain time period (e.g., up to about 20 seconds for auto-injectors, and about 10 minutes to about 60 minutes for an LVD). Other specifications can include a low or minimal level of discomfort, or to certain conditions related to human factors, shelf-life, expiry, biocompatibility, environmental considerations, etc. Such variations can arise due to various factors, such as, for example, a drug ranging in viscosity from about 1 cP to about 50 cP. Consequently, a drug delivery device will often include a hollow needle ranging from about 25 to about 31 Gauge in size. Common sizes are 17, 29 and 31 Gauge.

The delivery devices described herein can also include one or more automated functions. For example, one or more of needle insertion, medicament injection, and needle retraction can be automated. Energy for one or more automation steps can be provided by one or more energy sources. Energy sources can include, for example, mechanical, pneumatic, chemical, or electrical energy. For example, mechanical energy sources can include springs, levers, elastomers, or other mechanical mechanisms to store or release energy. One or more energy sources can be combined into a single device. Devices can further include gears, valves, or other mechanisms to convert energy into movement of one or more components of a device.

The one or more automated functions of an auto-injector may each be activated via an activation mechanism. Such an activation mechanism can include an actuator, for example, one or more of a button, a lever, a needle sleeve, or other activation component. Activation of an automated function may be a one-step or multi-step process. That is, a user may need to activate one or more activation components in order to cause the automated function. For example, in a one-step process, a user may depress a needle sleeve against their body in order to cause injection of a medicament. Other devices may require a multi-step activation of an automated function. For example, a user may be required to depress a button and retract a needle shield in order to cause injection.

In addition, activation of one automated function may activate one or more subsequent automated functions, thereby forming an activation sequence. For example, activation of a first automated function may activate at least two of needle insertion, medicament injection, and needle retraction. Some devices may also require a specific sequence of steps to cause the one or more automated functions to occur. Other devices may operate with a sequence of independent steps.

Some delivery devices can include one or more functions of a safety syringe, pen-injector, or auto-injector. For example, a delivery device could include a mechanical energy source configured to automatically inject a medicament (as typically found in an auto-injector) and a dose setting mechanism (as typically found in a pen-injector).

According to some embodiments of the present disclosure, an exemplary drug delivery device 10 is shown in FIGS. 1A & 1B. Device 10, as described above, is configured to inject a medicament into a patient's body. Device 10 includes a housing 11 which typically contains a syringe 18 containing the medicament to be injected and the components required to facilitate one or more steps of the delivery process. A cap 12 is also provided that can be detachably mounted to the housing 11. Typically, a user must remove cap 12 from housing 11 before device 10 can be operated.

As shown, housing 11 is substantially cylindrical and has a substantially constant diameter along the longitudinal axis A-A. The housing 11 has a distal region D and a proximal region P. The term "distal" refers to a location that is relatively closer to a site of injection, and the term "proximal" refers to a location that is relatively further away from the injection site.

Device 10 can also include a needle sleeve 19 coupled to housing 11 to permit movement of sleeve 19 relative to housing 11. For example, sleeve 19 can move in a longitudinal direction parallel to longitudinal axis A-A. Specifically, movement of sleeve 19 in a proximal direction can permit a needle 17 to extend from distal region D of housing 11.

Insertion of needle 17 can occur via several mechanisms. For example, needle 17 may be fixedly located relative to housing 11 and initially be located within an extended needle sleeve 19. Proximal movement of sleeve 19 by placing a distal end of sleeve 19 against a patient's body and moving housing 11 in a distal direction will uncover the distal end of needle 17. Such relative movement allows the distal end of needle 17 to extend into the patient's body. Such insertion is termed "manual" insertion as needle 17 is manually inserted via the patient's manual movement of housing 11 relative to sleeve 19.

Another form of insertion is "automated", whereby needle 17 moves relative to housing 11. Such insertion can be triggered by movement of sleeve 19 or by another form of activation, such as, for example, a button 13. As shown in FIGS. 1A & 1B, button 13 is located at a proximal end of housing 11. However, in other embodiments, button 13 could be located on a side of housing 11.

Other manual or automated features can include drug injection or needle retraction, or both. Injection is the process by which a bung 14 is moved from a proximal location within a syringe 18 to a more distal location within the syringe 18 in order to force a medicament from the syringe 18 through needle 17. In some embodiments, a drive spring (not shown) is under compression before device 10 is activated. A proximal end of the drive spring can be fixed within proximal region P of housing 11, and a distal end of the drive spring can be configured to apply a compressive force to a proximal surface of bung 14. Following activation, at least part of the energy stored in the drive spring can be applied to the proximal surface of bung 14. This compressive force can act on bung 14 to move it in a distal direction. Such distal movement acts to compress the liquid medicament within the syringe 18, forcing it out of needle 17.

Following injection, needle 17 can be retracted within sleeve 19 or housing 11. Retraction can occur when sleeve 19 moves distally as a user removes device 10 from a patient's body. This can occur as needle 17 remains fixedly located relative to housing 11. Once a distal end of sleeve 19 has moved past a distal end of needle 17, and needle 17 is covered, sleeve 19 can be locked. Such locking can include locking any proximal movement of sleeve 19 relative to housing 11.

Another form of needle retraction can occur if needle 17 is moved relative to housing 11. Such movement can occur if the syringe 18 within housing 11 is moved in a proximal direction relative to housing 11. This proximal movement can be achieved by using a retraction spring (not shown), located in distal region D. A compressed retraction spring, when activated, can supply sufficient force to the syringe 18 to move it in a proximal direction. Following sufficient retraction, any relative movement between needle 17 and housing 11 can be locked with a locking mechanism. In addition, button 13 or other components of device 10 can be locked as required.

FIG. 2A and FIG. 2B show a first example of a feedback mechanism 20 for an injection device, such as those described with reference to FIG. 1A and FIG. 1B. FIG. 2A and FIG. 2B show a plunger 21 of the injection device, which moves from the position shown in FIG. 2A to the position shown in FIG. 2B to dispense medicament during use of the injection device. In particular, the plunger 21 may push a bung into a syringe as the plunger 21 moves, and this may dispense medicament from the syringe, for example through a needle, as described with reference to FIG. 1A and FIG. 1B.

As illustrated, a drive spring 22 is provided to move the plunger 21. The drive spring 22 may be pre-loaded, and a release mechanism may be provided to release the plunger 21 such that the drive spring 22 can move the plunger 21 to dispense medicament, as described previously. A housing 23 of the injection device is partially shown in FIG. 2A and FIG. 2B.

As shown, the feedback mechanism 20 includes an arm 24 having a first end 25 that is pivotally mounted to a fixing 26 on the housing 23. The first end 25 of the arm 24 is pivotally mounted to the fixing 26 by pivot 27. A second end 28 of the arm 24 is attached to a fixing 29 on an adjacent part of the housing 23 via a delay element 30. A biasing member (not shown) is provided that urges the arm 24 to rotate about the pivot 27 in a clockwise direction in the view of FIG. 2A and FIG. 2B. The biasing member may be a torsion spring. Therefore, the biasing member urges the arm 24 to rotate about the pivot 27 and, as shown in FIG. 2A, before the injection device is used the arm 24 abuts the side of the plunger 21 and rotation is prevented. In this position, the arm 24 and delay element 30 are in a stable position.

However, when the plunger 21 has moved during delivery of medicament the plunger 21 moves out of engagement with the arm 24 and then only the delay element 30 prevents rotation of the arm 24 about the pivot 27. In particular, the rotational force of the biasing member places the delay element 30 under a tensile load and, as shown in FIG. 2B, this tensile load is sufficient to break the delay element 30 and allow the arm 24 to rotate.

The rotation of the arm 24 provides user feedback. In particular, the arm 24 may rotate such that a part of the arm 24 contacts the side of the plunger 21 and/or a part of the drive spring 22. This impact can create a sound or tactile effect that provides the user with feedback. In other examples, the rotation of the arm 24 may close a switch, or the arm 24 may move into a visible position, to provide user feedback. In this example, the arm 24, and the housing 23 and/or drive spring 22 that it impacts, form an indicator that generates user feedback, as explained.

As explained above, a tensile load is applied to the delay element 30, and the delay element 30 is broken to permit rotation of the arm 24. The delay element 30 is configured so that it breaks at a time after the tensile load is applied, to create a delay between the plunger 21 disengaging from the arm 24 and the user feedback being generated.

In particular, the delay element 30 is designed to have material creep tendencies, so that the tensile load slowly deforms and elongates the delay element 30 before fracturing and allowing rotation of the arm 24. This creates a time delay between the load being applied to the delay element 30 and the delay element 30 being broken so that user feedback is generated.

In this example, the arm 24 and the plunger 21 are arranged such that the plunger 21 disengages from the arm 24 once all or nearly all of the medicament has been injected. In this way, the tensile load is only placed on the delay element 30 at or towards the end of the injection. The further delay before the user feedback is generated, which is provided by the delay element 30, provides time for the medicament to disperse from the injection site.

The delay element 30 may be attached to the fixing 29 by clamping, welding, or adhering, or another suitable form of attachment, depending on the materials used and the form of the delay element 30.

As illustrated in FIG. 3A, a first example of the delay element 30 includes a narrow section 31 having a smaller cross-section than the ends 32 of the delay element 30. The narrow section 31 is configured to be the part of the delay element 30 that is broken by the tensile load applied to the delay element 30 during use.

The duration of the delay provided by the delay element 30 will depend on several factors, including the cross-section of the narrow section 31, the force applied, and the material properties of the delay element 30. Different delay elements, with different cross-sectional areas, can be provide for devices and medicaments having different characteristics, for example delivery dose size or medicament viscosity.

Figure 3B:
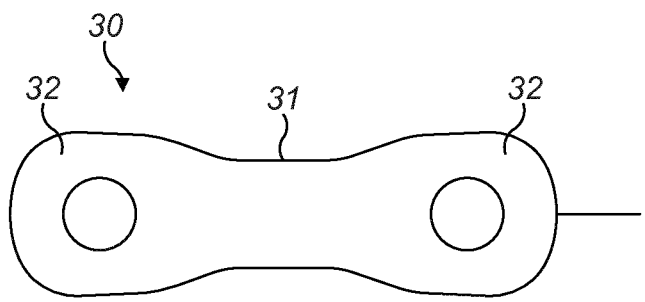

FIG. 3B shows another example delay element 30, having a narrow section 31 with a larger cross-sectional area than the narrow section 31 of the example of FIG. 3A. If the materials and tensile load are the same, then this delay element 30 will create a longer delay than the delay element 30 of FIG. 3A because more material has to be broken to release the arm 24.

For the examples of FIG. 3A and FIG. 3B, it is preferable to select a material with viscoelastic creep properties, so that the tensile load will break the delay element 30 without the need for a high impact force.

Examples of suitable materials are polymers, such as polyethylene (PE), polypropylene (PP), polytetrafluoroethylene (PTFE), polyethylene terephthalate (PET).

In other examples, the delay element 30 may be made of a deformable material that does not fracture after being elongated by the force applied during use. In this way, the delay element 30 will deform under the tensile load of the biasing member, allowing the arm 24 to rotate, which can generate user feedback as explained previously. In this example, the delay element 30 may be an elastic band, or the delay element 30 may include an elastomer, for example a rubber such as isobutylene isoprene butyl, acrylonitrile butadiene, or silicone rubber. The delay element 30 may be elastically or plastically deformable.

Figure 3C:
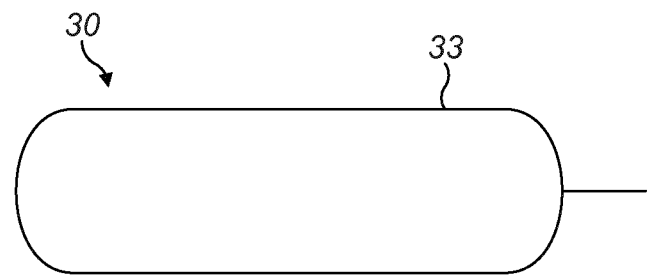

FIG. 3C shows an example of such a deformable delay element 30, in the form of a band 33 of elastomeric material that is wrapped around the fixing 29 on the housing 23 and also around the second end 28 of the arm 24. After the plunger 21 has moved to dispense medicament, the tensile load provided by the biasing member stretches the deformable delay element 30 until the user feedback is generated. The deformable delay element 30 retards the rotational movement of the arm 24, creating a delay before the user feedback is generated.

Figure 4B:
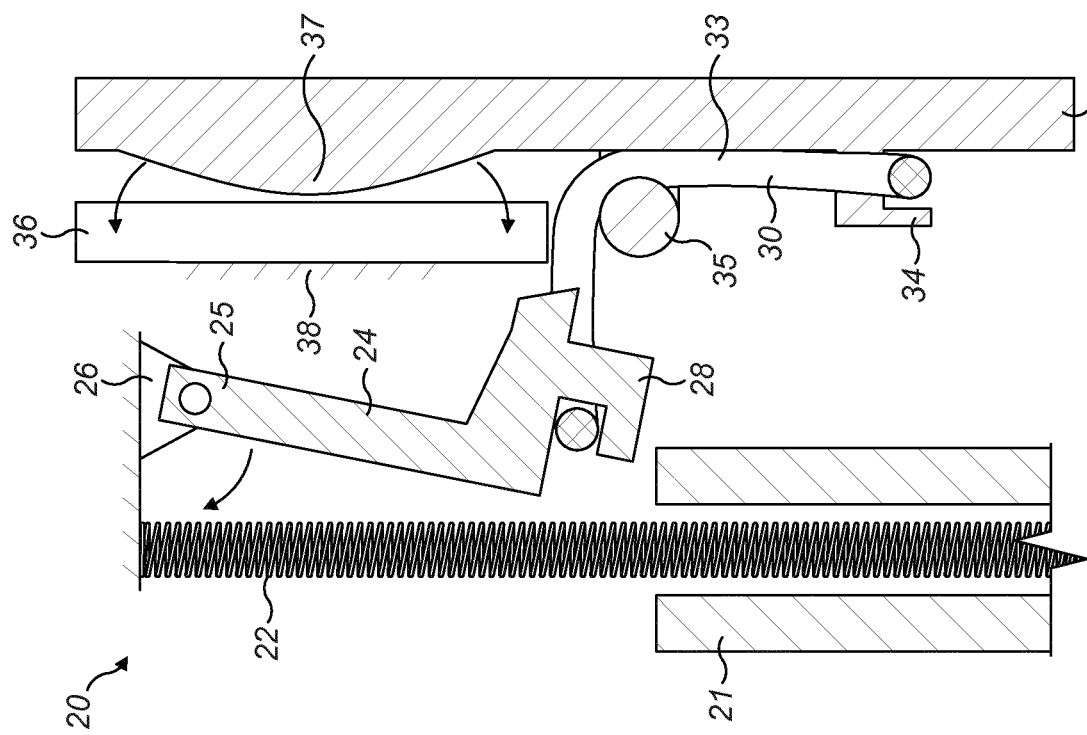
FIG. 4B is a cross-section side view of the delay mechanism of FIG. 4A, shown after the injection device has been used.
Figure 4A:
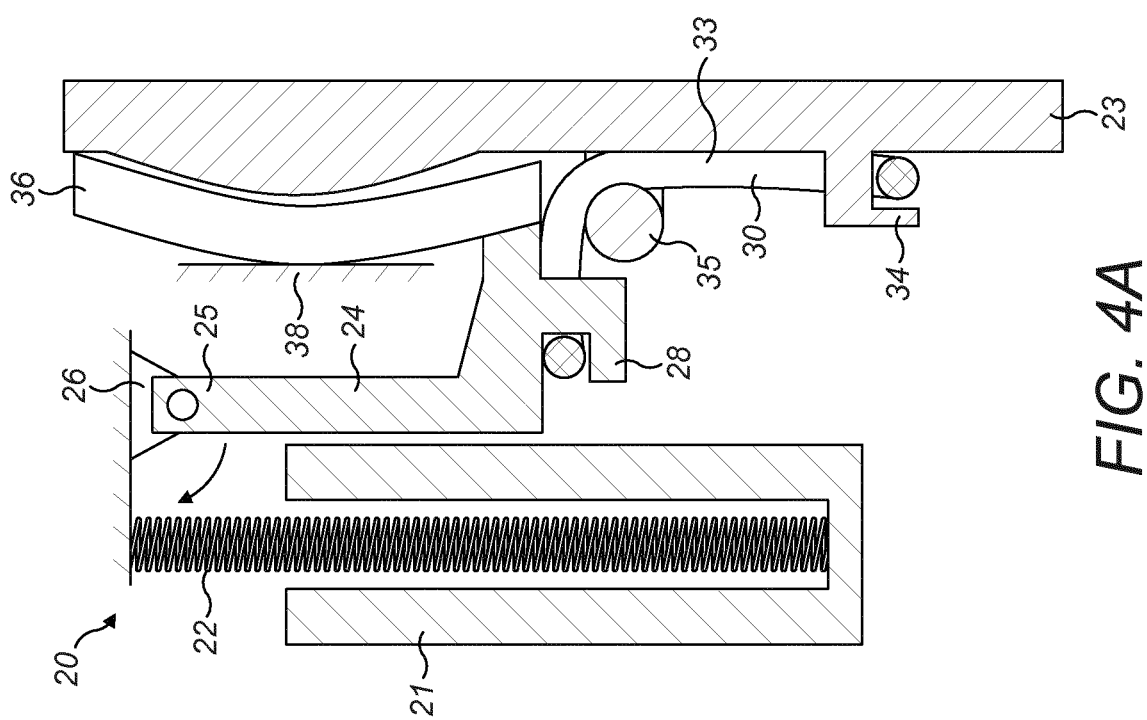
FIG. 4A is a cross-sectional side view of a delay mechanism for an injection device, the delay mechanism having a pivotally mounted arm and a delay element, the delay mechanism shown before the injection device has been used.

FIG. 4A and FIG. 4B show a similar example feedback mechanism 20 for an injection device to that of FIG. 2A and FIG. 2B, with a plunger 21 that is moved by a drive spring 22 to dispense medicament from the injection device, and an arm 24 pivotally mounted to the housing 23. The first end 25 of the arm 24 is pivotally mounted to a fixing 26 on the housing 23, and a biasing member (not shown) applies a rotational force to the arm 24 to urge the arm 24 in a clockwise direction as shown in FIG. 4A and FIG. 4B. The biasing member may be a torsion spring.

In this example, an adjacent part of the housing 23 has a fixing 34 and a bar 35, and a delay element 30 attaches the arm 24 to the fixing 34 and extends around the bar 35. In particular, the delay element 30 is bent or wrapped over the bar 35, the fixing 34 and the second end 28 of the arm 24. In this example, the delay element 30 is a band 33 of deformable material, similar to that shown in FIG. 3C, for example an elastomeric material. The ends of the band 33 are wrapped about the fixing 34 and the second end 28 of the arm 24, with the band 33 being wrapped over the bar 35.

As shown in FIG. 4A, in the initial position the plunger 21 prevents the arm 24 from rotation, while the arm 24 holds a sound generator 36 in a deflected state.

The sound generator 36 is a pre-stressed element that is initially held in a deflected state (FIG. 4A) and then moves into a non-deflected state (FIG. 4B) when the arm 24 releases the sound generator 36. As illustrated, the housing 23 includes a protrusion 37 against which the arm 24 presses the sound generator 36 to cause it to be held in a deflected state until the arm 24 releases the sound generator 36. A retaining member 38 is positioned to hold the sound generator 36 in position. This change of state of the sound generator 36 generates an audible sound, for example a clicking sound, which provides the user feedback. In this example, the sound generator 36 is an indicator that generates the user feedback.

Therefore, once the plunger 21 moves to dispense medicament, the arm 24 is released and rotates, the sound generator 36 is released and generates user feedback. The rotation of the arm 24 is retarded by the delay element 30, which has to be stretched for the arm 24 to rotate sufficiently to release the sound generator 36.

In this example, the delay element 30 may be an elastic band 33, as explained above, or the delay element 30 may alternatively include an elastomer, for example a rubber such as isobutylene isoprene butyl, acrylonitrile butadiene, or silicone rubber.

In this example, the arm 24 and the plunger 21 are arranged such that the plunger 21 disengages from the arm 24 once all or nearly all of the medicament has been injected. In this way, the tensile load is only placed on the delay element 30 at or towards the end of the injection. The further delay before the user feedback is generated, which is provided by the delay element 30, provides time for the medicament to disperse from the injection site.

In an alternative example, the delay element 30 may be configured to break under the force provided through rotation of the arm 24.

In an alternative example, the sound generator 36 may provide the biasing force urging the arm 24 to rotate, and so there is no need for the additional biasing member acting on the arm 24.

Figure 5B:
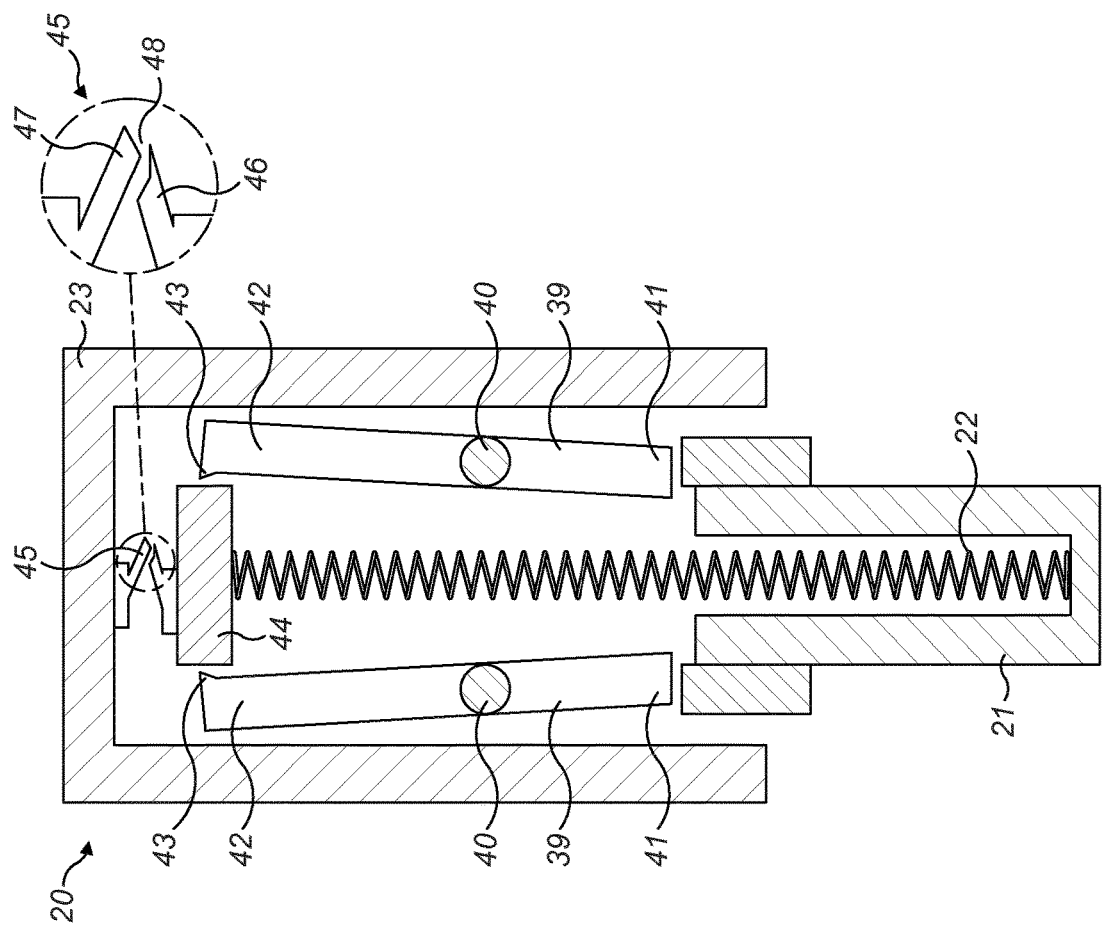
FIG. 5B is a cross-section side view of the delay mechanism of FIG. 5A, shown after the injection device has been used.
Figure 5A:
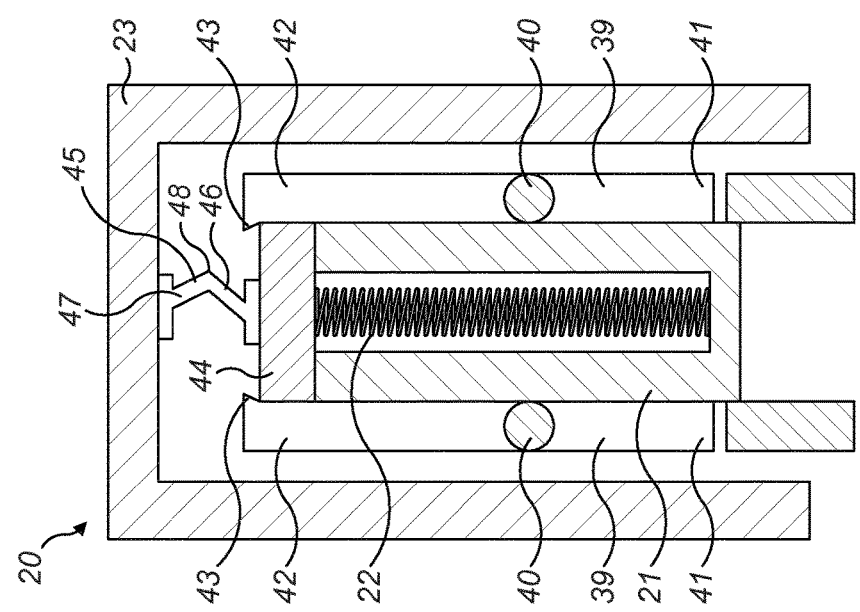
FIG. 5A is a cross-sectional side view of a delay mechanism for an injection device, the delay mechanism having a carrier and a breakable delay element, the delay mechanism shown before the injection device has been used.

FIG. 5A and FIG. 5B show another example of a delay mechanism 20 for an injection device, the injection device including a plunger 21 and a drive spring 22 that moves the plunger 21 to dispense medicament during use of the injection device.

In this example, locking arms 39 are mounted on pivots 40 either side of the plunger 21 so that the plunger 21 prevents rotation of the locking arms 39 until the plunger 21 has been moved past the ends 41 of the locking arms 39 as it dispenses medicament.

Proximal ends 42 of the locking arms 39 include deflections 43 that engage and hold a plate 44. The drive spring 22 acts between the plate 44 and the plunger 21, urging them apart so that the plunger 21 moves to dispense medicament.

However, as illustrated to FIG. 5B, once the drive spring 22 has pushed the plunger 21 past the ends 41 of the locking arms 39, the locking arms 39 are free to rotate and the force of the drive spring 22, acting through the plate 44 against the inward deflections 43, causes the locking arms 39 to rotate and release the plate 44. The drive spring 22 now urges the plate 44 in a proximal direction.

A delay element 45 is disposed between the plate 44 and the housing 23 of the injection device, on an opposite side of the plate 44 to the drive spring 22. Therefore, once the plate 44 is released by the locking arms 39 the force of the drive spring 22 compresses the delay element 45.

As illustrated, the delay element 45 is configured to deform and then break under the compressive force of the drive spring 22, and the breaking of the delay element 45 can generate an audible sound, providing user feedback. In this example, the delay element 45 is an indicator that generates user feedback when it is broken.

The delay element 45 does not break immediately on release of the plate 44 by the locking arms 39, so a delay is created between the end of the medicament dispensing (plunger 21 releasing locking arms 39) and the feedback being provided to the user (delay element 45 breaking).

The delay element 45 may comprise a polymer, such as polyethylene (PE), polypropylene (PP), polytetrafluoroethylene (PTFE), polyethylene terephthalate (PET). Alternatively, the delay element 45 may comprise a metal, for example steel or copper.

As illustrated, the delay element 45 comprises a pair of opposed angled plates 46, 47, arranged to define a point 48 where they join. In this way, when the compressive load is applied the delay element 45 is folded about this point 48 until the material at the point 48 fractures, generating user feedback.

The delay element 45 of this example is configured to break at a time after the compressive load is placed upon the delay element 45, so that a delay is created between the plunger 21 releasing the locking arms 39 and the user feedback being generated. The delay may be during deformation of the delay element 45, before the delay element 45 is fractured.

Figure 6B:
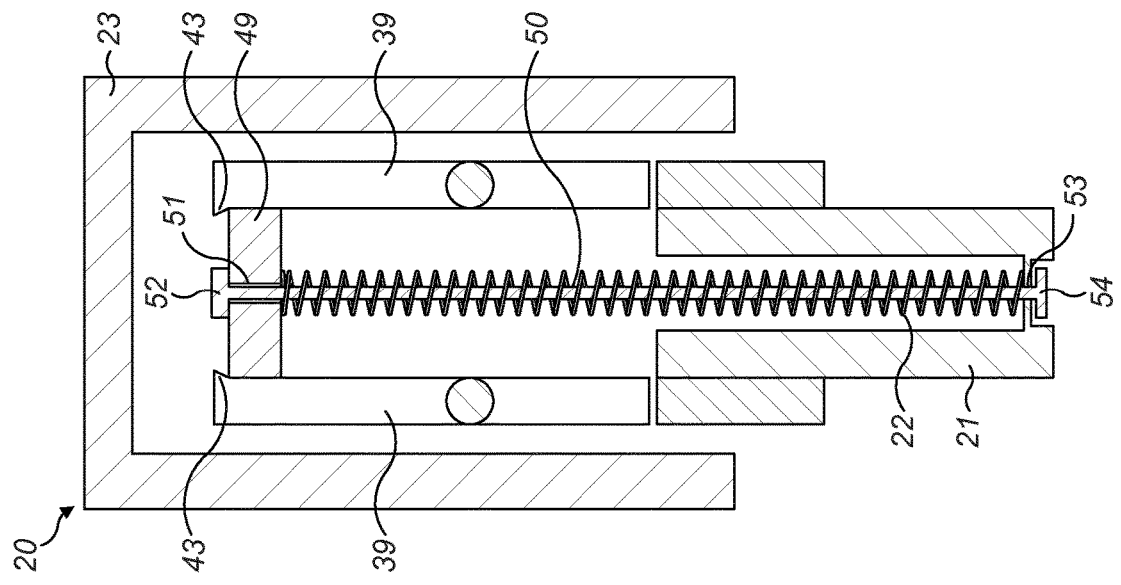
FIG. 6B is a cross-section side view of the delay mechanism of FIG. 6A, shown during use of the injection device.
Figure 6A:
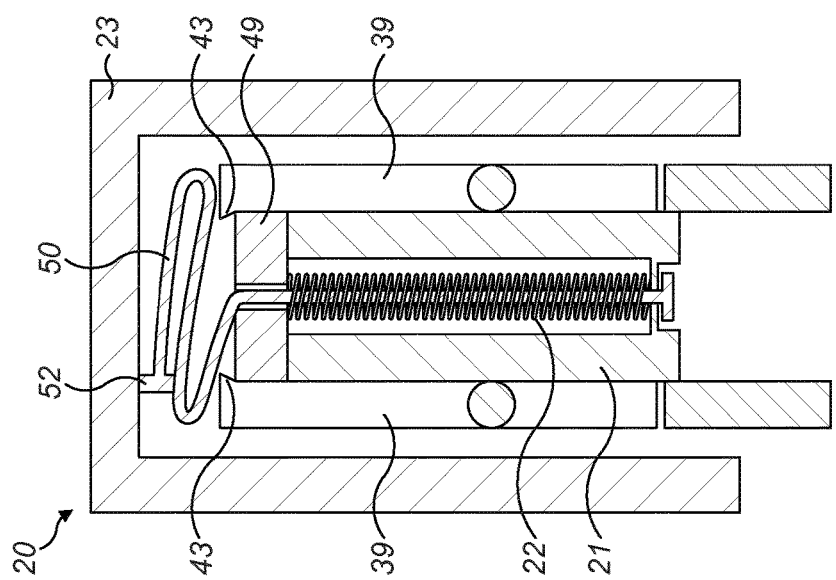
FIG. 6A is a cross-sectional side view of a delay mechanism for an injection device, the delay mechanism having a carrier and a breakable tether that is a delay element, the delay mechanism shown before the injection device has been used.
Figure 6C:
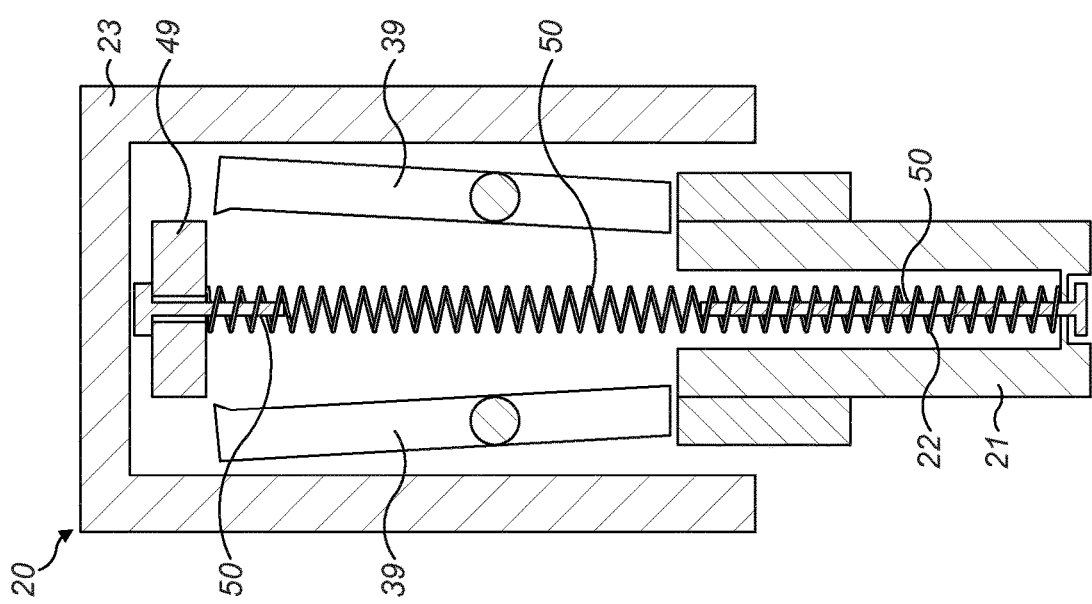
FIG. 6C is a cross-section side view of the delay mechanism of FIG. 6A and FIG. 6B, shown after the injection device has been used.

FIG. 6A, FIG. 6B, and FIG. 6C show a further example feedback mechanism 20 for an injection device, similar to that of FIG. 5A and FIG. 5B. In particular, as shown in FIG. 6A the injection device comprises a plunger 21 and a drive spring 22 is arranged to move the plunger 21 to dispense medicament. Locking arms 39 and a plate 49 are arranged similarly to the example of FIG. 5A and FIG. 5B, with the plate 49 being pushed by the drive spring 22 and gripped by the locking arms 39 (via inward deflections 43) until the plunger 21 moves past the locking arms 39 (FIG. 6B), which then rotate and release the plate 49 (FIG. 6C).

In this example, a delay element 50 joins the plunger 21 to the plate 49. In particular, as shown, the delay element 50 is a tether that extends from the plate 49 to the plunger 21, and is joined to both. The tether 50 is flexible, akin to rope or string. The tether 50 extends through a hole 51 in the plate 49 and a retaining part 52 is provided on the other side, and the tether 50 extends through a hole 53 in the plunger 21 and a retaining part 54 is provided on the other side.

Therefore, after the plate 49 is released by the locking arms 39 the force of the drive spring 22 is entirely applied to the tether 50. The tether 50 is placed under tension and, after a delay, the tether 50 breaks as shown in FIG. 6C.

The tether 50 may be stretched, deformed, prior to breaking, or it may break under the tensile load without elongation. When the tether 50 breaks the plate 49 is pushed distally against the inside of the housing 23 and the impact between the plate 49 and the housing 23 generates audible and/or tactile feedback for the user. In this example, the plate 49, and the housing 23 that it impacts, together form an indicator that generates user feedback.

The tether 50 of this example is configured to break at a time after the tensile load is placed upon the tether 50, so that a delay is created between the plunger 21 releasing the locking arms 39 and the user feedback being generated. The tether 50 may be made of a material having a creep tendency, so that a part of the tether 50 deforms and stretches before failing and breaking. The tether 50 may include a weakened region, for example a thinned region, designed to fail after a pre-determined time under the tensile load of the drive spring 22.

The tether 50 may comprise a flexible polymer, and may be made of wound fibres. For example, the tether 50 may comprise nylon, polyester, polypropylene or polyethylene fibres.

As the plate 49 is only released after the plunger 21 has moved past the locking arms 39, the user feedback is provided at a time after medicament has been injected during use of the injection device. Therefore, the delay can provide time for the medicament to disperse from the injection site before user feedback is generated, at which time the user knows to remove the injection device.

In an alternative example, the tether 50 deforms until the plate 49 reaches the housing 23. Once the plate 49 abuts the housing 23 the plate 49 may contact a switch, or it may become visible to the user, thereby providing user feedback.

Figure 7A:
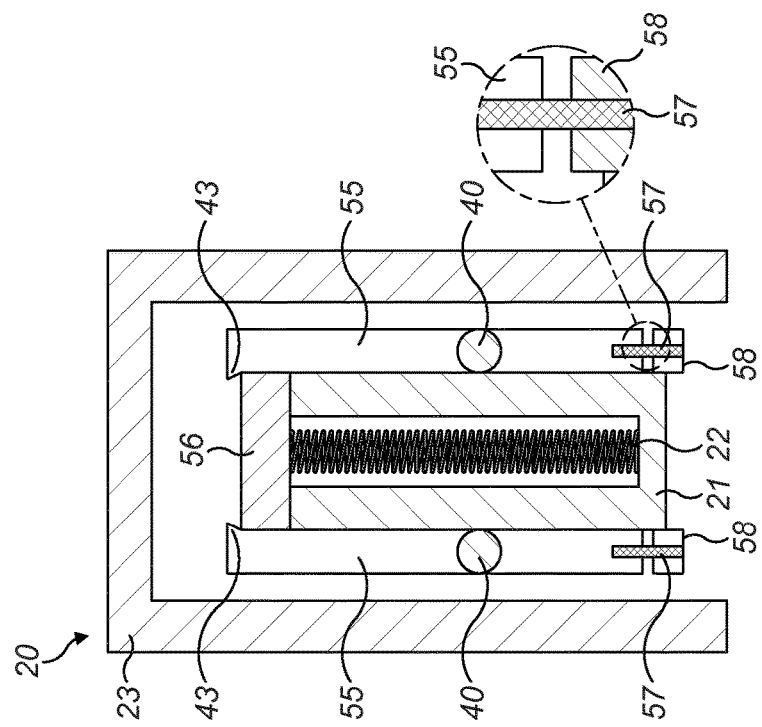
FIG. 7A is a cross-sectional side view of a delay mechanism for an injection device, the delay mechanism having a carrier and rotatable arms with integrated delay elements, the delay mechanism shown before the injection device has been used.
Figure 7C:
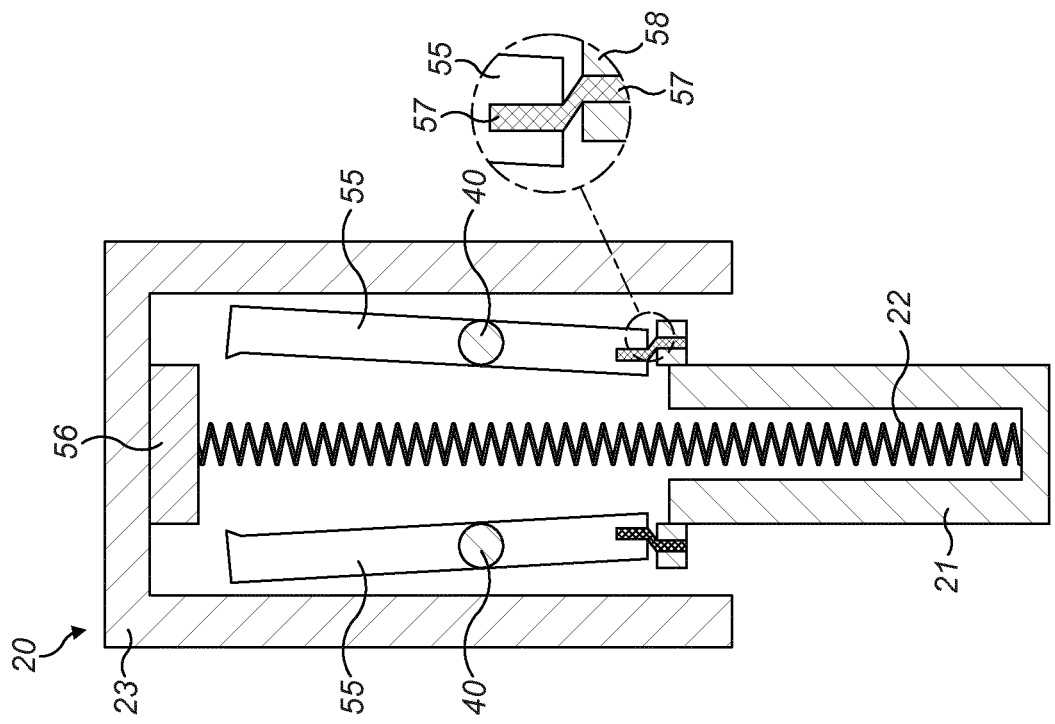
FIG. 7B is a cross-section side view of the delay mechanism of FIG. 7A, shown during use of the injection device; and, FIG. 7C is a cross-section side view of the delay mechanism of FIG. 7A and FIG. 7B, shown after the injection device has been used.
Figure 7B:
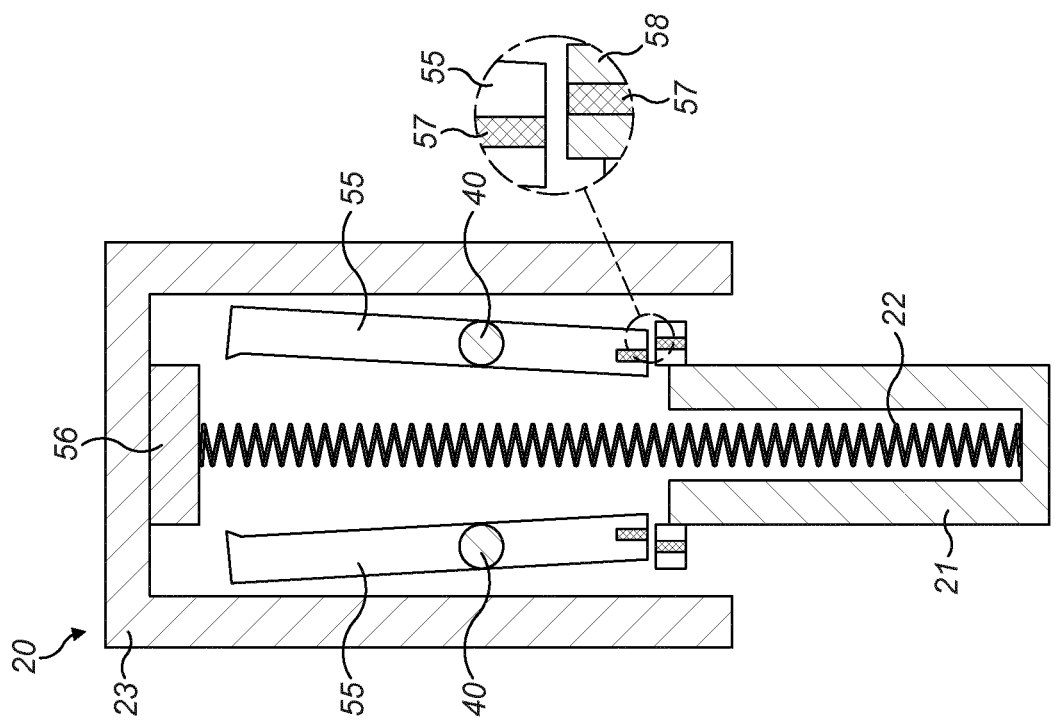

FIG. 7A, FIG. 7B and FIG. 7C show further example feedback mechanisms 20 for an injection device. As shown in FIG. 7A the injection device comprises a plunger 21 and a drive spring 22 is arranged to move the plunger 21 to dispense medicament. Locking arms 55 and a plate 56 are arranged similarly to the example of FIG. 5A and FIG. 5B, with the plate 56 being pushed by the drive spring 22 and gripped by the locking arms 55 (via inward deflections 43) until the plunger 21 moves past the locking arms 55, which then rotate and release the plate 56, as shown in FIG. 7B and FIG. 7C.

In this example, delay elements 57 are provided between the locking arms 55 and a part 58 of the housing 23 of the injection device. In particular, as shown in FIG. 7A, delay elements 57 extend between an end of each locking arm 55 and an adjacent part 58 of the housing 23. These act to delay rotation of the locking arms 55 once the plunger 21 has moved past them.

As shown in FIG. 7B and FIG. 7C, after the arms 55 rotate the plate 56 is released and pushed distally by the drive spring 22 against the inside of the housing 23 and the impact between the plate 56 and the housing 23 generates audible and/or tactile feedback for the user. In this example, the plate 56, and the housing 23 that it impacts, together form an indicator that generates user feedback.

In the example of FIG. 7B, the delay elements 57 are broken by the shear force applied on the delay elements 57 by the locking arms 55 as the drive spring 22 and plate 56 urge the locking arms 55 to rotate. That is, after the plunger 21 has moved past the locking arms 55 the force of the drive spring 22 urges the plate 56 against the inward deflections 43, which urges the locking arms 55 to rotate about the pivots 40. This applies a shear load on the delay elements 57.

The delay elements 57 are configured to break under this shear load, after a delay. The delay elements 57 may comprise a polymer, such as polyethylene (PE), polypropylene (PP), polytetrafluoroethylene (PTFE), polyethylene terephthalate (PET). Alternatively, the delay element 57 may comprise a metal, for example steel or copper. The delay elements 57 may comprise a foil that is broken by the shear load.

In the example of FIG. 7C, the delay elements 57 are deformed by the shear force applied on the delay elements 57 by the locking arms 55 as the drive spring 22 and plate 56 urge the locking arms 55 to rotate. That is, after the plunger 21 has moved past the locking arms 55 the force of the drive spring 22 urges the plate 56 against the inward deflections 43, which urges the locking arms 55 to rotate about the pivots 40. This applies a shear load on the delay elements 57. The delay elements 57 need only deform enough to allow the locking arms 55 to rotate enough for the plate 56 to move past the inward deflections 43.

The delay elements 57 are configured to deform under this shear load, after a delay. The delay elements 57 may comprise a polymer, such as polyethylene (PE), polypropylene (PP), polytetrafluoroethylene (PTFE), polyethylene terephthalate (PET). Alternatively, the delay element 57 may comprise a metal, for example steel or copper. The delay elements 57 may comprise a foil that is deformed by the shear load.

The delay created between the plunger 21 moving past the locking arms 55 and the plate 56 being released, provided by the delay elements 57, allows time for the medicament to disperse from the injection site before the user feedback indicates that the injection device can be removed from the user.

In alternative examples, similar to those described with reference to FIG. 5A-5B, FIG. 6A-6C, and FIG. 7A-7C, a biasing member may be provided to urge the locking arms 39, 55 to rotate. The plunger 21 prevents rotation of the locking arms 39, 55 until the plunger 21 has moved past the locking arms 39, 55, and the biasing member applies a force to the delay element(s) 45, 50, 57. The biasing member may be a torsion spring. After the delay element 45, 50, 57 is deformed and/or broken the biasing member causes the locking arms 39, 55 to rotate and impact the housing 23, generating audible and/or tactile user feedback. This biasing member acting on the locking arms 39, 55 may be provided in addition to, or instead of, the plate(s) 44, 49, 56 described with reference to FIG. 5A-5B, FIG. 6A-6C, and FIG. 7A-7C.

In each of the examples described herein a force is applied to a delay element 30, 45, 50, 57, which is broken and/or deformed after a delay. The delay elements 30, 45, 50, 57 are configured to provide a predictable and repeatable delay, or a minimum delay. The duration of the delay may be selected based on the type of injection device, the properties of the medicament being injected, and other such factors.

In various examples, the duration of the delay may be greater than 2 seconds, or greater than 5 seconds, or greater than 10 seconds, or greater than 20 seconds, or greater than 30 seconds. In other examples, the duration of the delay may be between 5 seconds and 30 seconds, or the delay may be between 5 seconds and 20 seconds, or the delay may be between 5 seconds and 15 seconds. In yet further examples, the duration of the delay may be less than 1 minute, or less than 45 seconds, or less than 30 seconds.

The terms "drug" or "medicament" are used herein to describe one or more pharmaceutically active compounds. As described below, a drug or medicament can include at least one small or large molecule, or combinations thereof, in various types of formulations, for the treatment of one or more diseases. Exemplary pharmaceutically active compounds may include small molecules; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more of these drugs are also contemplated.

The term "drug delivery device" shall encompass any type of device or system configured to dispense a drug into a human or animal body. Without limitation, a drug delivery device may be an injection device (e.g., syringe, pen injector, auto injector, large-volume device, pump, perfusion system, or other device configured for intraocular, subcutaneous, intramuscular, or intravascular delivery), skin patch (e.g., osmotic, chemical, micro-needle), inhaler (e.g., nasal or pulmonary), implantable (e.g., coated stent, capsule), or feeding systems for the gastro-intestinal tract. The presently described drugs may be particularly useful with injection devices that include a needle, e.g., a small gauge needle.

The drug or medicament may be contained in a primary package or "drug container" adapted for use with a drug delivery device. The drug container may be, e.g., a cartridge, syringe, reservoir, nor other vessel configured to provide a suitable chamber for storage (e.g., short- or long-term storage) of one or more pharmaceutically active compounds. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of a drug formulation (e.g., a drug and a diluent, or two different types of drugs) separately, one in each chamber. In such instances, the two chambers of the dual-chamber cartridge may be configured to allow mixing between the two or more components of the drug or medicament prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drug delivery devices and drugs described herein can be used for the treatment and/or prophylaxis of many different types of disorders. Exemplary disorders include, e.g., diabetes mellitus or complications associated with diabetes mellitus such as diabetic retinopathy, thromboembolism disorders such as deep vein or pulmonary thromboembolism. Further exemplary disorders are acute coronary syndrome (ACS), angina, myocardial infarction, cancer, macular degeneration, inflammation, hay fever, atherosclerosis and/or rheumatoid arthritis.

Exemplary drugs for the treatment and/or prophylaxis of diabetes mellitus or complications associated with diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the term "derivative" refers to any substance which is sufficiently structurally similar to the original substance so as to have substantially similar functionality or activity (e.g., therapeutic effectiveness).

Exemplary insulin analogues are Gly(A21), Arg(B31), Arg(B32) human insulin (insulin glargine); Lys(B3), Glu (B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Exemplary insulin derivatives are, for example, B29-N-myristoyl-des(B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin; B29-N-(N-lithocholyl-gamma-glutamyl)-des(B30) human insulin; B29-N-(ω-carboxyheptadecanoyl)-des(B30) human insulin and B29-N-(ω-carboxyhepta-decanoyl) human insulin. Exemplary GLP-1, GLP-1 analogues and GLP-1 receptor agonists are, for example: Lixisenatide/AVE0010/ZP10/ Lyxumia, Exenatide/Exendin-4/Byetta/Bydureon/ITCA 650/AC-2993 (a 39 amino acid peptide which is produced by the salivary glands of the Gila monster), Liraglutide/ Victoza, Semaglutide, Taspoglutide, Syncria/Albiglutide, Dulaglutide, rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An exemplary oligonucleotide is, for example: mipomersen/Kynamro, a cholesterol-reducing antisense therapeutic for the treatment of familial hypercholesterolemia.

Exemplary DPP4 inhibitors are Vildagliptin, Sitagliptin, Denagliptin, Saxagliptin, Berberine.

Exemplary hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Exemplary polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20/Synvisc, a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region.

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful include, for example, Fab fragments, F(ab')2 fragments, scFv (single-chain Fv) fragments, linear antibodies, monospecific or multispecific antibody fragments such as bispecific, trispecific, and multispecific antibodies (e.g., diabodies, triabodies, tetrabodies), minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen.

Exemplary antibodies are anti PCSK-9 mAb (e.g., Alirocumab), anti IL-6 mAb (e.g., Sarilumab), and anti IL-4 mAb (e.g., Dupilumab).

The compounds described herein may be used in pharmaceutical formulations comprising (a) the compound(s) or pharmaceutically acceptable salts thereof, and (b) a pharmaceutically acceptable carrier. The compounds may also be used in pharmaceutical formulations that include one or more other active pharmaceutical ingredients or in pharmaceutical formulations in which the present compound or a pharmaceutically acceptable salt thereof is the only active ingredient. Accordingly, the pharmaceutical formulations of the present disclosure encompass any formulation made by admixing a compound described herein and a pharmaceutically acceptable carrier.

Pharmaceutically acceptable salts of any drug described herein are also contemplated for use in drug delivery devices. Pharmaceutically acceptable salts are for example acid addition salts and basic salts. Acid addition salts are e.g. HCl or HBr salts. Basic salts are e.g. salts having a cation selected from an alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are known to those of skill in the arts.

Pharmaceutically acceptable solvates are for example hydrates or alkanolates such as methanolates or ethanolates.

Those of skill in the art will understand that modifications (additions and/or removals) of various components of the substances, formulations, apparatuses, methods, systems and embodiments described herein may be made without departing from the full scope and spirit of the present invention, which encompass such modifications and any and all equivalents thereof.

The invention claimed is:

1. A feedback mechanism for an injection device, the injection device configured to deliver a medicament to a user, the feedback mechanism comprising:
   a delay element;
   a biasing member configured to apply a force to the delay element, wherein the delay element is configured to be deformed and/or broken by the force at a time after the force is applied by the biasing member;
   an indicator configured to generate user feedback after the delay element is deformed and/or broken; and
   a restraining element configured to be moveable from a first position, in which the restraining element prevents the delay element from being deformed and/or broken by the force of the biasing member, to a second position, in which the delay element is deformed and/or broken by the force of the biasing member applied to the delay element.

2. The feedback mechanism of claim 1, wherein the delay element comprises a member having a narrow section configured to be deformed and/or broken by the force of the biasing member.

3. The feedback mechanism of claim 1, wherein the delay element comprises a deformable member configured to be deformed and/or broken by the force of the biasing member.

4. The feedback mechanism of claim 1, wherein the delay element comprises a flexible tether configured to be deformed and/or broken by the force of the biasing member.

5. The feedback mechanism of claim 1, wherein the feedback mechanism comprises a moveable member, and wherein the delay element is attached to the moveable member and to a fixing, and wherein the biasing member is configured to urge the moveable member relative to the fixing such that the force is applied to the delay element.

6. The feedback mechanism of claim 5, wherein the moveable member comprises an arm pivotally mounted to a pivot, and the biasing member is configured to urge the arm to rotate about the pivot.

7. The feedback mechanism of claim 5, wherein the moveable member comprises a plate, and the biasing member is configured to act on the plate.

8. The feedback mechanism of claim 5, wherein the indicator comprises a sound generator configured to be impacted by the moveable member after the delay element is deformed and/or broken to generate a sound.

9. The feedback mechanism of claim 5, wherein the indicator comprises a pre-stressed element disposed such that the moveable member holds the pre-stressed element in a deflected state until the moveable member is moved, at which point the pre-stressed element moves to a non-deflected state and generates the user feedback.

10. The feedback mechanism of claim 5, further comprising a holding mechanism configured to hold the moveable member such that the delay element is prevented from being deformed or broken, and wherein the holding mechanism is further configured to release the moveable member so that the delay element can be deformed and/or broken by the force of the biasing member.

11. The feedback mechanism of claim 10, wherein the holding mechanism is configured to release the moveable member after the injection device has completed delivery of medicament to the user.

12. An injection device comprising:
   a medicament delivery mechanism comprising:
      a reservoir; and
      a plunger configured to move during use from a first position to a second position to displace medicament from the reservoir for delivery to a user during use of the injection device; and
   a feedback mechanism comprising:
      a delay element;
      a biasing member configured to apply a force to the delay element, wherein the delay element is configured to be deformed and/or broken by the force at a time after the force is applied by the biasing member;
      an indicator configured to generate user feedback after the delay element is deformed or broken; and
      a restraining element configured to be moveable from a first position, in which the restraining element prevents the delay element from being deformed and/or broken by the force of the biasing member, to a second position, in which the delay element is deformed and/or broken by the force of the biasing member applied to the delay element.

13. The injection device of claim 12, wherein the feedback mechanism comprises a moveable member that is attached to the delay element, and wherein the biasing member is configured to apply a force to the moveable member such that the force is applied to the delay element.

14. The injection device of claim 13, wherein the plunger is arranged such that in the first position the plunger engages the moveable member to prevent movement of the moveable member, and in the second position the plunger disengages the moveable member.

15. The injection device of claim 13, wherein the delay element is attached to the moveable member and to a fixing.

16. The injection device of claim 13, wherein the delay element is attached to the moveable member and to the plunger.

17. The injection device of claim 13, wherein the moveable member comprises a plate, and the biasing member is configured to act on the plate.

18. The injection device of claim 17, further comprising a locking arm configured to engage the plate, the locking arm being pivotally mounted such that in the first position the plunger prevents rotation of the locking arm and the plate is retained by the locking arm, and in the second position the locking arm is free to rotate and release the plate.

19. The injection device of claim 18, wherein the delay element is configured to resist rotation of the locking arm until the delay element is deformed and/or broken.

20. The injection device of claim 12, wherein the reservoir contains the medicament.

21. A method of using an injection device, the method comprising:

delivering a medicament to a user;

applying a force to a delay element using a biasing member to deform and/or break the delay element by moving a restraining element from a first position, in which the restraining element prevents the delay element from being deformed and/or broken by the force of the biasing member, to a second position, in which the delay element is deformed and/or broken by the force of the biasing member applied to the delay element; and generating user feedback after the delay element has been deformed and/or broken;

wherein a delay is provided such that the delay element is deformed and/or broken at a time after the force is applied.

* * * * *